(12) United States Patent
He et al.

(10) Patent No.: US 8,614,337 B2
(45) Date of Patent: Dec. 24, 2013

(54) S-5-SUBSTITUENT-N-2'-(THIOPHENE-2-YL)ETHYL-TETRALIN-2-AMINE OR CHIRAL ACID SALTS THEREOF AND USE FOR PREPARING ROTIGOTINE

(75) Inventors: Xungui He, Shanghai (CN); Jianping Guo, Shanghai (CN); Yanling Wang, Shanghai (CN); Wensheng Tang, Shanghai (CN); Xingzhong Zhang, Shanghai (CN); Xuezhang Wang, Shanghai (CN); Yuan Wang, Shanghai (CN)

(73) Assignee: 2Y-Chem Ltd., Shanghai (CN)

( * ) Notice: Subject to any disclaimer, the term of this patent is extended or adjusted under 35 U.S.C. 154(b) by 0 days.

(21) Appl. No.: 13/394,614

(22) PCT Filed: Sep. 7, 2010

(86) PCT No.: PCT/CN2010/001360
§ 371 (c)(1),
(2), (4) Date: Apr. 18, 2012

(87) PCT Pub. No.: WO2011/026318
PCT Pub. Date: Mar. 10, 2011

(65) Prior Publication Data
US 2013/0046100 A1 Feb. 21, 2013

(30) Foreign Application Priority Data

Sep. 7, 2009 (CN) .......................... 2009 1 0195260

(51) Int. Cl.
*C07D 333/20* (2006.01)
*C07D 333/22* (2006.01)

(52) U.S. Cl.
USPC .............................................. 549/77; 549/75

(58) Field of Classification Search
USPC ....................................................... 549/75, 77
See application file for complete search history.

(56) References Cited

U.S. PATENT DOCUMENTS

| | | | |
|---|---|---|---|
| 4,410,519 A | 10/1983 | Seiler et al. | |
| 4,931,270 A | 6/1990 | Horn et al. | |
| 4,968,837 A | 11/1990 | Manimaran et al. | |
| 5,382,596 A | 1/1995 | Sleevi et al. | |
| 6,372,920 B1 | 4/2002 | Minaskanian et al. | |
| 2011/0313176 A1 | 12/2011 | Khunt et al. | |

(Continued)

FOREIGN PATENT DOCUMENTS

| | | |
|---|---|---|
| EP | 0 168 505 | 1/1986 |
| WO | 2009/056791 A1 | 5/2009 |
| WO | WO 2010/073124 | 7/2010 |

OTHER PUBLICATIONS

International Search Report for PCT/CN2010/001360, mailed Dec. 16, 2010.

Ames et al., "The Synthesis of Alkoxy-1,2,3,4-tetrahydronaphthalene Derivatives. Part I. 2-Amino-, Alkylamino-, and Dialkylamino-derivatives", *J. Chem. Soc.*, pp. 2636-2641 (1965).
"N-0923", *Drugs of the Future*, 18(11):1005-1008 (1993).
Li et al., "Advances in the Chiral Drug Resolutions", *Chinese Journal of New Drugs*, 14(8):969-974 (2005) (Abstract).
Communication dated Feb. 11, 2013 and Extended EP Search Report for corresponding EP Application No. 10813240.8, dated Jan. 23, 2013, 7 pages.

*Primary Examiner* — Kristin Vajda
(74) *Attorney, Agent, or Firm* — Nixon & Vanderhye, PC

(57) ABSTRACT

The chiral compound S-5-substituted-N-2'-(thienyl-2-yl-)ethyl-tetralin-2-amine or its chiral acid salts and preparation method thereof are disclosed, and the method for preparing Rotigotine by using the chiral compound is also disclosed. Racemic 5-substituted-N-2'-(thien-2-yl-)ethyl-tetralin-2-amine (compound 1) is resolved by using a conventional chiral acid to obtain an optically pure chiral acid salt of S-5-substituted-N-2'-(thien-2-yl-)ethyl-tetralin-2-amine, which is then dissociated to obtain S-5-substituted-N-2'-(thien-2-yl-)ethyl-tetralin-2-amine (compound 2). The compound 2 or chiral acid salt thereof is alkylated and deprotected to produce rotigotine (compound 5).

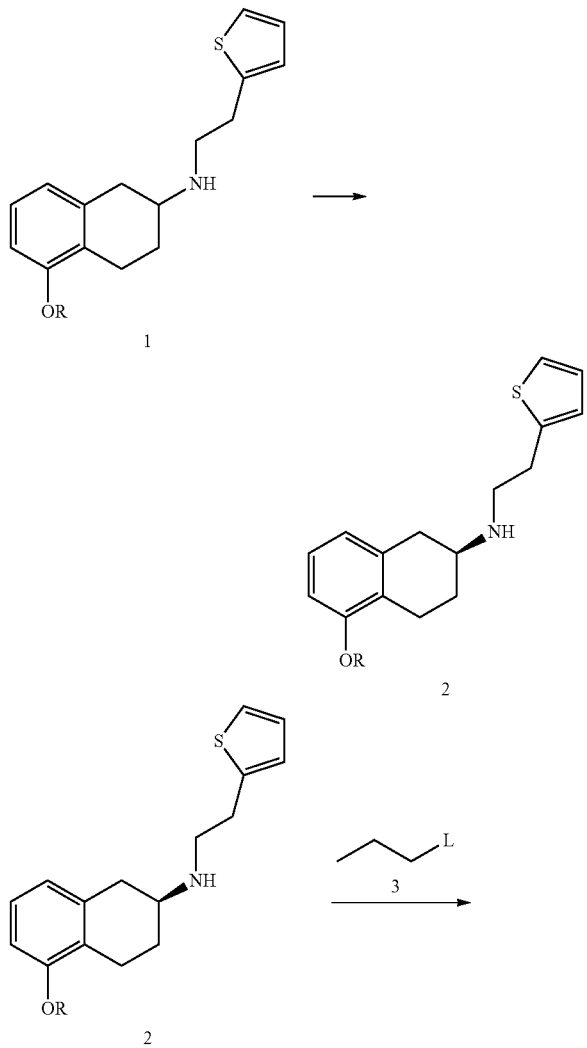

-continued
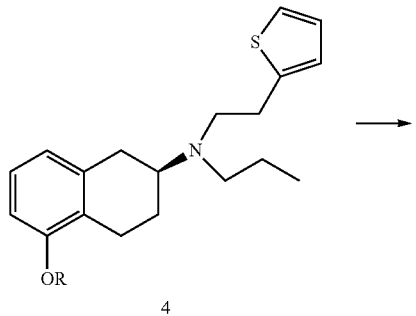
4
-continued
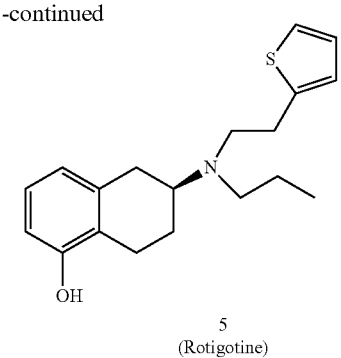
5
(Rotigotine)
21 Claims, No Drawings

S-5-SUBSTITUENT-N-2'-(THIOPHENE-2-YL)ETHYL-TETRALIN-2-AMINE OR CHIRAL ACID SALTS THEREOF AND USE FOR PREPARING ROTIGOTINE

This application is the U.S. national phase of International Application No. PCT/CN2010/001360 filed 7 Sep. 2010 which designated the U.S. and claims priority to CN 200910195260.8 filed 7 Sep. 2009, the entire contents of each of which are hereby incorporated by reference.

FIELD OF THE INVENTION

The present invention relates to the field of pharmaceutical chemistry, and more precisely to a new chiral compound S-5-substituted-N-2'-(thien-2-yl-)ethyl-tetralin-2-amine or its chiral acid salts as well as a method for preparing the same, and a method for preparing rotigotine a drug for treating Parkinson's disease, by using the same.

BACKGROUND OF THE INVENTION

According to statistics, there are about 4 million patients suffering from Parkinson's disease (PD) throughout the world now, wherein about 1.5 million patients are in the United States. The main clinical manifestation of PD includes difficulty to walk, tremor, dyskinesia, rigidity, bradykinesia, and incapability of being in equilibrium. Any age of person may be affected with PD, and the average age of onset is 60 years old. About five to ten percent of the patients are young patients whose age of onset is 40 years old or less. About five to ten percent of the patients have positive family history, which means genes can play a certain role in the pathogenic mechanism of PD.

There is a phenomenon in the PD patients that a large number of cells secreting dopamine in brain are damaged or died, resulting in the related dyskinesia. Dopamine agonist is an important drug for treating Parkinson's disease, and can produce a neurotransmitter that is important for motor function by simulating the action of dopamine so as to ameliorate symptoms. Rotigotine was developed by Schwarz Biosciences in Germany for the auxiliary therapy of the early successive Parkinson's disease and later Parkinson's disease, commercialized under the trademark name of Neupro, and approved to come into the market by FDA on May, 2007. Neupro was the first transdermal patch for the treatment of Parkinson's disease. The clinical research showed that administering once daily could maintain a steady drug level in 24-hour via percutaneous permeation.

Generally, the synthesis of rotigotine comprises the steps of reduction-amination of 5-methoxy-2-tetralone with n-propylamine, salt resolution, acylation, reduction, demethylation, and salt purification, etc. (Drugs Fut, 1993, 18, (11): 1005; J Chem Soc, 1965, 2636-41; U.S. Pat. No. 4,968,837). This synthetic route requires a plural of steps with a low yield. Especially, the steps of the acylation and the following reduction relate to a relatively complicated reaction, and may cause racemization of partial intermediates, resulting in a low yield of the whole synthetic route. Moreover, the reducing agent is expensive, which makes rotigotine quite expensive.

Ever since a long time ago, the synthetic process of rotigotine has being optimized. It is disclosed in U.S. Pat. No. 5,382,596, U.S. Pat. No. 4,410,519, U.S. Pat. No. 6,372,920 and WO2009/056791 that the product of the reduction-amination of 5-methoxy-2-tetralone with n-propylamine is directly subjected to an alkylation with 2-thienylethyl, instead of the previous acylation and reduction, wherein the alkylating agent is 2-thienylethane with a leaving group. The main differences among these alkylation methods are that the leaving group of 2-thienylethane and the optimization for operation are different.

It is a pity that all the yields of the above variously optimized processes are not satisfied, among them, the highest is only 55%. Moreover, the purification procedure requires using column chromatography. The overall efficiencies of the above processes are very low, although the starting materials can be recovered. In addition, all the above optimized processes are based on the alkylation following the introduction of a leaving group to 2-thienylethane, which increases the reaction procedures.

SUMMARY OF INVENTION

The present inventors made efforts to optimize the process for synthesizing rotigotine. In this study, a new chiral compound S-5-substituted-N-2'-(thien-2-yl-)ethyl-tetralin-2-amine or its chiral acid salt is successfully obtained by resolution, and then alkylated, and deprotected to simply and conveniently prepare rotigotine, a drug for treating Parkinson's disease. The method has a low cost and is easy to be industrialized.

Therefore, it is one object of the present invention to provide a chiral compound S-5-substituted-N-2'-(thien-2-yl-)ethyl-tetralin-2-amine represented by the following Formula 2, or its chiral acid salts.

It is another object of the present invention to provide a method for preparing the above chiral compound or its chiral acid salts.

It is still another object of the present invention to provide a method for preparing rotigotine using the above chiral compound or a chiral acid salt thereof.

In one aspect, the present invention provides a S-5-substituted-N-2'-(thien-2-yl-)ethyl-tetralin-2-amine represented by the following Formula 2, or its chiral acid salts:

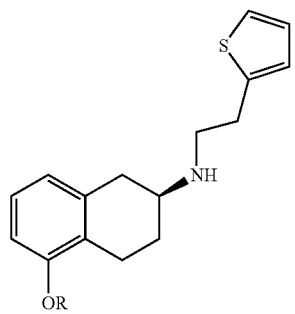

2 wherein

R is $C_1$-$C_6$ lower alkyl or $C_1$-$C_6$ lower fatty acyl. The alkyl may be, for example, methyl, ethyl, propyl, isopropyl, or butyl, or the like, and preferably methyl.

The chiral acid salt may be, for example, a L-(+)-tartrate of the S-5-substituted-N-2'-(thien-2-yl-)ethyl-tetralin-2-amine, its structure formula is below:

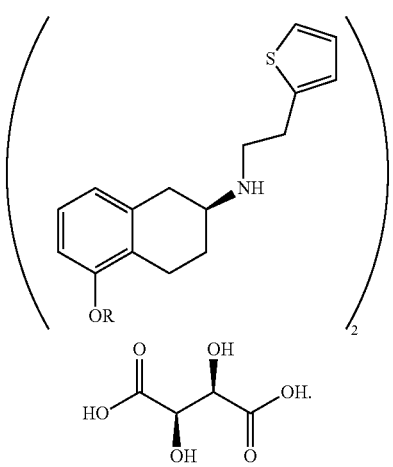

In another aspect, the present invention provides a method for preparing the above chiral compound or its chiral acid salts, comprising the steps of:

resolving a racemic 5-substituted-N-2'-(thien-2-yl-)ethyl-tetralin-2-amine (i.e. compound 1) by using a conventional chiral acid, for example L-(+)-mandelic acid or L-(+)-tartaric acid, to obtain an optically pure chiral acid salt of 5-substituted-N-2'-(thien-2-yl-)ethyl-tetralin-2-amine in S configuration (i.e. a chiral acid salt of compound 2); and dissociating the chiral acid salt of the 5-substituted-N-2'-(thien-2-yl-)ethyl-tetralin-2-amine in S configuration under an alkaline condition to obtain an optically pure compound 2 in S configuration. The reaction scheme is as follows:

Among others, the resolution step using the chiral acid is specifically performed as follows.

A solution of compound 1 is obtained by dissolving a racemic 5-substituted-N-2'-(thien-2-yl-)ethyl-tetralin-2-amine (i.e. compound 1) in a solvent, wherein the solvent may be acetone, methanol, ethanol, water, or a mixed solvent thereof, and preferably a mixed solvent of acetone and water, wherein the volume ratio of acetone to water is generally 1:1 to 10:1, and preferably 4:1 to 7.5:1.

A solution of a chiral acid is obtained by dissolving the acid in a solvent, wherein the solvent may be preferably acetone, water, or a mixed solvent thereof, and the chiral acid is generally L-(+)-mandelic acid or L-(+)-tartaric acid.

The solution of the chiral acid is added dropwisely into the solution of compound 1 at a temperature of 20-30° C., wherein the molar ratio of the chiral acid to the compound 1 is 0.2:1-1:1, and preferably 0.5:1-0.7:1, and stirred for three hours or more to precipitate a solid, which is filtered and washed to afford an optically pure chiral acid salt of a 5-substituted-N-2'-(thien-2-yl-)ethyl-tetralin-2-amine in S configuration (i.e. a chiral acid salt of compound 2).

The above prepared chiral acid salt of 5-substituted-N-2'-(thien-2-yl-)ethyl-tetralin-2-amine in S configuration may be further purified by recrystallization, for example, using a mixed solvent of acetone and water in any ratio.

The dissociation of S-5-methoxy-N-2'-(thien-2-yl-)ethyl-tetralin-2-amine can be achieved by dissociating the 5-substituted-N-2'-(thien-2-yl-)ethyl-tetralin-2-amine in S configuration with a base such as sodium hydroxide, sodium carbonate, potassium carbonate, and the like in an organic solvent such as a mixed solvent system of dichloromethane and water or that of ethyl acetate and water.

Among them, compound 1 may be prepared by referring to U.S. Pat. No. 4,931,270 through the reduction-amination of 5-R-2-tetralone with 2-thienyl ethylamine.

In still another aspect, the present invention provides a method for preparing rotigotine using the S-5-substituted-N-2'-(thien-2-yl-)ethyl-tetralin-2-amine or its chiral acid salts, which comprises the steps of: carrying out an alkylation reaction of compound 2 or its chiral acid salt with compound 3 using a base catalyst in a solvent to give compound 4 (i.e., (S)-5-substituted-N-propyl-N-(2'-(thien-2-yl-)ethyl)-tetralin-2-amine) which can be further salified with an acid; and removing the protecting group R from compound 4 or its salt to give compound 5 Rotigotine. The main reaction scheme is as follows:

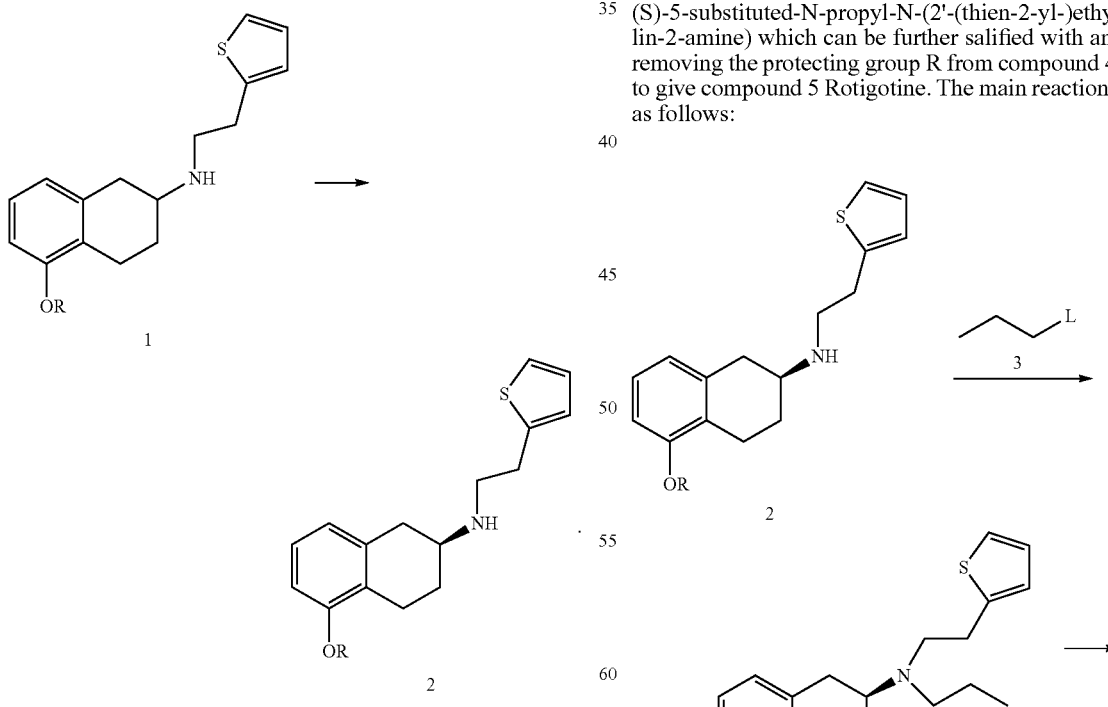

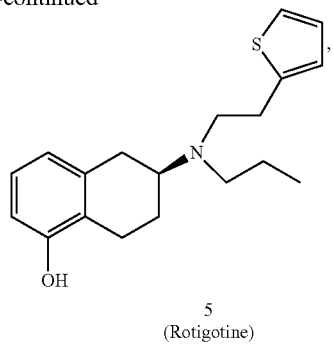

5
(Rotigotine)

wherein compound 3 is propane with a leaving group, L represents the leaving group and may be halogen such as chlorine, bromine or iodine; or alkylsulfonyl or arylsulfonyl such as methylsulfonyl, trifluoromethylsulfonyl, ethylsulfonyl, benzenesulfonyl, tosyl, parachlorobenzenesulfonyl, nitrobenzenesulfonyl, methoxybenzenesulfonyl, or the like.

The solvent used in the alkylation reaction may be a low polar solvent such as dichloromethane and toluene, or may be a high polar solvent such as tetrahydrofuran, methyltetrahydrofuran, acetone, butanone, N,N-dimethylformamide, N,N-dimethylacetamide, N-methylpyrrolidone, dimethyl sulfoxide, water or any combination thereof.

Compound 4 can be synthesized by directly reacting the chiral acid salt of compound 2 with compound 3 under an alkaline condition, or by dissociating a chiral acid salt of compound 2 under an alkaline condition and then reacting with compound 3.

The base catalyst used for the synthesis of compound 4 may be an organic base such as triethylamine, diisopropylethylamine, pyridine, N,N-dimethylaminopyridine, 2,6-dimethylpyridine, N-methylmorpholine, 1,8-diazabicyclo[5.4.0]undec-7-ene (DBU), 1,5-diazabicyclo[4.3.0]nonyl-5-ene (DBN), and the like, or may also be an inorganic base such as sodium carbonate, potassium carbonate, sodium bicarbonate, sodium hydroxide, potassium hydroxide, potassium phosphate, and the like.

A phase transfer catalyst can be introduced into the synthetic reaction of compound 4 to accelerate the reaction and promote the reaction complete. The used phase transfer catalyst may be tetrabutylammonium chloride, tetrabutylammonium bromide, tetrabutylammonium iodide, tetrabutylammonium bisulfate, benzyltrimethylammonium chloride, benzyltriethylammonium chloride, trioctylmethylammonium chloride, 18-crown ether-6 or diphenyl-18-crown ether-6, or the like.

In the step of removing the protecting group R from compound 4 or its salt to give compound 5 rotigotine, a deprotection agent, for example boron tribromide, AlCl$_3$, or the like, can be added into the organic solution of compound 4, followed by stirring at a temperature of from −30° C. to room temperature until the reaction is complete.

Rotigotine can be further purified. Rotigotine may be formed into a salt with an acid and dissociated after the purification to give pure rotigotine.

In the steps of purifying rotigotine by salt formation with an acid, the acid may be an inorganic acid such as hydrochloric acid, hydrobromic acid, sulphuric acid, phosphoric acid, and the like; or may also be an organic acid such as methane sulfonic acid, 4-methylbenzenesulfonic acid, formic acid, acetic acid, oxalic acid, succinic acid, fumaric acid, maleic acid, and the like.

Advantageous Effects

The present invention uses the starting materials that are commercially available and easily obtained without being further modified, and shortens the synthetic route. The current synthetic routes have a low efficiency of resolution and crystallization and needs to recrystallize three to four times to give the purer intermediate chiral amine with low yield. However, the present invention only needs one recrystallization to obtain the chiral amine (i.e. compound 2) with the optical purity of 96% or more, and its yield is relative high. The optically pure compound 2 is subjected to the consequent reactions to finally give rotigotine with the optical purity of 99.5% or more, thereby shortening the production period and lowering the production cost.

BEST MODE FOR CARRYING OUT THE INVENTION

The following examples are provided to assist a person in the art in fully understanding the invention without restricting the scope of the invention in any way.

Preparation Example 1

Preparation of 5-methoxy-N-2'-(thien-2-yl-)ethyl-tetralin-2-amine (Compound 1)

To a 20 L reactor, the pre-prepared NaBH(AcO)$_3$ (1600.62 g, 7.77 mol) and dichloromethane (DCM) (7.45 kg) were added at room temperature under nitrogen (N$_2$) atmosphere, and the interior temperature was cooled to 20° C. or less. In another 10 L three-necked flask, 2-thienyl ethylamine (538.8 g, 4.24 mol) was added to a solution of 5-methoxy-2-tetralone (622 g, 3.53 mol) in DCM (3.2 kg) at room temperature. The mixed solution in the 10 L three-necked flask was added dropwisely to the 20 L reactor at 20° C. or less. After the addition, glacial acetic acid (450 g, 7.5 mol) was added dropwisely thereto and then the mixture was stirred at room temperature overnight. The reaction was quenched with water under ice water bath. The pH of the reaction mixture was adjusted to be alkaline by dropwise addition of 50% aqueous sodium hydroxide (NaOH) solution. The organic phase was separated out. The water layer was extracted with DCM, and the organic phases were combined and concentrated to give 5-methoxy-N-2'-(thien-2-yl-)ethyl-tetralin-2-amine with a chemical purity of 96% and a yield of 98%. (NaBH(AcO)$_3$ was self-made by suspending sodium borohydride in DCM, dropwisely adding 3 equivalents of acetic acid thereto, and stirring for 24 hours or more.)

$^1$H-NMR (400 MHz, CDCl$_3$): δ 7.16 (m, 1H, aromatic), 7.10 (m, 1H, aromatic), 6.95 (m, 1H, aromatic), 6.85 (m, 1H, aromatic), 6.70 (m, 2H, aromatic), 3.81 (s, 3H, —OMe), 2.9 (m, 6H, —CH$_2$—, —CH—), 2.60 (m, 2H, —CH$_2$—), 2.05 (m, 1H, —CH$_2$—), 1.54 (m, 2H, —CH$_2$—).

Preparation Example 2

Preparation of 5-methoxy-N-2'-(thien-2-yl-)ethyl-tetralin-2-amine (Compound 1)

5-methoxy-2-tetralone (1 g, 5.68 mmol) and 2-thienyl ethylamine (3 g, 23.6 mmol) were dissolved in 150 mL of tetrahydrofuran (THF). The reaction was carried out for 16 hours at 55° C. by adding 10% palladium carbon (0.1 g) and introducing hydrogen gas with a pressure of 3 MPa. After the reaction was complete, the hydrogen gas was released. The reaction liquid was filtered and evaporated to dryness to give 5-methoxy-N-2'-(thien-2-yl-)ethyl-tetralin-2-amine.

Nuclear magnetic resonance data are the same as those of the above Preparation Example 1.

Example 1

Preparation of S-5-methoxy-N-2'-(thien-2-yl-)ethyl-tetralin-2-amine L-(+)-tartrate (Chiral Acid Salt of Compound 2)

The above prepared 5-methoxy-N-2'-(thien-2-yl-)ethyl-tetralin-2-amine (2 g, 7 mmol) was dissolved in 20 mL of acetone and 20 mL of methanol. 4.5 mL aqueous solution of L-(+)-tartaric acid (0.47 g, 3.5 mmol) was added dropwisely thereto. The reaction solution was stirred at a temperature of 20-30° C. for one hour, and concentrated under reduced pressure. The residual oil was dissolved with 15 mL acetone to make it clear, and stirred at a temperature of 20-30° C. overnight. The reaction mixture was filtered, and the filter cake was washed with acetone and dried at room temperature to gave S-5-methoxy-N-2'-(thien-2-yl-)ethyl-tetralin-2-amine L-(+)-tartrate with an optical purity of 70% and a yield of 48%.

The measured optical rotation is: S-5-methoxy-N-2'-(thien-2-yl-)ethyl-tetralin-2-amine L-(+)-tartrate: $[\alpha_d^{20}]$ (c=1, 6N HCl/acetonitrile=15/85)=−50.1°.

$^1$H-NMR (400 MHz, CDCl$_3$): δ 7.34 (m, 1H, aromatic), 7.07 (m, 1H, aromatic), 7.0 (m, 2H, aromatic), 6.73 (m, 1H, aromatic), 6.68 (m, 1H, aromatic), 3.91 (s, 1H, tartaric acid, —CO—CH—O), 3.74 (s, 3H, —OMe), 3.0 (m, 6H, —CH$_2$—, —CH—), 2.77 (m, 1H, —CH$_2$—), 2.67 (m, 1H, —CH$_2$—), 2.50 (m, 1H, —CH$_2$—), 2.10 (m, 1H, —CH$_2$—), 1.60 (m, 1H, —CH$_2$—).

Example 2

Preparation of S-5-methoxy-N-2'-(thien-2-yl-)ethyl-tetralin-2-amine L-(+)-tartrate (Chiral Acid Salt of Compound 2)

The above prepared 5-methoxy-N-2'-(thien-2-yl-)ethyl-tetralin-2-amine (1 g, 3.5 mmol) was dissolved in 5 mL of ethanol. L-(+) tartaric acid (0.105 g, 0.7 mmol) was dissolved in 1 mL of water, and slowly dropped with the above ethanol solution. A solid were precipitated under stirring at room temperature and filtered. The filter cake was washed with ethanol and dried at room temperature to gave S-5-methoxy-N-2'-(thien-2-yl-)ethyl-tetralin-2-amine L-(+)-tartrate with an optical purity of 70% and a yield of 10%.

Nuclear magnetic resonance data and optical rotation are the same as those of the above Example 1.

Example 3

Preparation of S-5-methoxy-N-2'-(thien-2-yl)ethyl-tetralin-2-amine L-(+)-tartrate (Chiral acid salt of Compound 2)

The above prepared 5-methoxy-N-2'-(thien-2-yl-)ethyl-tetralin-2-amine (50 g, 0.17 mol) was dissolved in 150 mL of acetone and 20 mL of water. L-(+) tartaric acid (11.75 g, 75 mmol) was dissolved in a mixture solution of 5 mL of water and 75 mL of acetone, and slowly dropped with the above acetone solution. A solid were precipitated by stirring at room temperature and filtered. The filter cake was washed with acetone (0.5 mL×2) and dried at room temperature to gave S-5-methoxy-N-2'-(thien-2-yl-)ethyl-tetralin-2-amine L-(+)-tartrate with an optical purity of 70% and a yield of 40%.

Nuclear magnetic resonance data and optical rotation value are the same as those of the above Example 1.

Example 4

Recrystallization of S-5-methoxy-N-2'-(thien-2-yl-)ethyl-tetralin-2-amine L-(+)-tartrate (Chiral Acid Salt of Compound 2)

At room temperature, the above prepared crude S-5-methoxy-N-2'-(thien-2-yl-)ethyl-tetralin-2-amine L-(+)-tartrate (10.67 g, 14.73 mmol) was dissolved in acetone (160 mL)/water (64 mL), and heated under reflux for 0.5 hour. The mixture was cooled naturally to room temperature and filtered. The filter cake was dried to give optically pure S-5-methoxy-N-2'-(thien-2-yl-)ethyl-tetralin-2-amine L-(+)-tartrate. The above step of recrystallization may be repeated until the optical purity reaches to 96% or more, when necessary. Yield: 50%.

Example 5

Dissociation of S-5-methoxy-N-2'-(thien-2-yl-)ethyl-tetralin-2-amine

At room temperature, the S-5-methoxy-N-2'-(thien-2-yl-)ethyl-tetralin-2-amine L-(+)-tartrate (330 g, 0.46 mol) prepared above in Example 4 was suspended in 1 L DCM and 1 L water. The mixture was stirred at room temperature (25° C.) for 10-15 minutes. The interior temperature was cooled to a temperature of 10° C.-15° C. The pH was adjusted to 12-13 by dropwise addition of 10% aqueous sodium hydroxide (NaOH) solution. The organic phase was separated out. The water layer was extracted with DCM (4.2 L×2) twice, and the organic phases were combined, washed once with water and 5% aqueous sodium chloride solution respectively, and dried over anhydrous magnesium sulfate. After filtration, the filtrate was concentrated to dryness to give S-5-methoxy-N-2'-(thien-2-yl-)ethyl-tetralin-2-amine with an optical purity of 96% and a yield of 100%.

The measured optical rotation is: S-5-methoxy-N-2'-(thien-2-yl-)ethyl-tetralin-2-amine free base: $[\alpha_d^{20}]$(c=0.43, DCM)=−44.4°.

$^1$H-NMR (400 MHz, CDCl$_3$): δ 7.17 (m, 1H, aromatic), 7.13 (m, 1H, aromatic), 7.0 (m, 1H, aromatic), 6.89 (m, 1H, aromatic), 6.74 (m, 1H, aromatic), 6.69 (m, 1H, aromatic), 3.83 (s, 3H, —OMe), 3.0 (m, 7H, —CH$_2$—, —CH—), 2.62 (m, 2H, —CH$_2$—), 2.10 (m, 1H, —CH$_2$—), 1.60 (m, 1H, —CH$_2$—).

Example 6

Preparation of (S)-5-methoxy-N-propyl-N-(2'-(thien-2-yl-)ethyl)-tetralin-2-amine (Compound 4)

A 250 mL three-necked reaction flask was equipped with a mechanical agitator, a thermometer and a condenser, and protected under nitrogen from the top of the condenser. The S-5-methoxy-N-2'-(thien-2-yl-)ethyl-tetralin-2-amine (10 g, 34.8 mmol) prepared above in Example 5, iodopropane (11.83 g, 69.6 mmol), NaHCO$_3$ (5.8 g, 69.6 mmol) and DMF (50 mL) were added thereto at room temperature, and heated to 85° C. to react overnight. After cooling to room temperature, 100 mL ethyl acetate and 100 mL water were added, and the mixture was left alone and partitioned. The organic phases were washed with a saturated aqueous sodium chloride solution twice and concentrated to give a crude oily (S)-5-methoxy-N-propyl-N-(2'-(thien-2-yl-)ethyl)-tetralin-2-amine with a purity of 96% and a yield of 95%, which may be directly used for the next step without further purification.

Example 7

Preparation of (S)-5-methoxy-N-propyl-N-(2'-(thien-2-yl-)ethyl)-tetralin-2-amine hydrochloride (Hydrochloride of Compound 4)

A 500 mL three-necked reaction flask was equipped with a magnetic stirrer, a thermometer and a condenser, and protected under nitrogen from the top of the condenser. The S-5-methoxy-N-2'-(thien-2-yl-)ethyl-tetralin-2-amine L-(+)-tartrate (1 g, 1.4 mmol) prepared above in Example 4, iodopropane (0.72 g, 4.2 mmol), $Na_2CO_3$ (0.47 g, 5.6 mmol) and DMF (50 mL) were added thereto at room temperature, and heated to a temperature of 95-98° C. to react overnight. After cooling to room temperature, 100 mL of ethyl acetate and 100 mL of water were added, and the organic layer was separated out. The organic phases were washed with saturated aqueous sodium chloride solution, added with concentrated hydrochloric acid to form a salt, and then concentrated to dryness to give (S)-5-methoxy-N-propyl-N-(2'-(thien-2-yl-)ethyl)-tetralin-2-amine hydrochloride with a purity of 96% and a yield of 95%.

Example 8

Preparation of (S)-5-methoxy-N-propyl-N-(2'-(thien-2-yl-)ethyl)-tetralin-2-amine Hydrochloride (Hydrochloride of Compound 4)

A 500 mL three-necked reaction flask was equipped with a magnetic stirrer, a thermometer and a condenser, and protected under nitrogen from the top of the condenser. The S-5-methoxy-N-2'-(thien-2-yl-)ethyl-tetralin-2-amine L-(+)-tartrate (1 g, 1.4 mmol) prepared above in Example 4, iodopropane (0.72 g, 4.2 mmol), $Na_2CO_3$ (0.47 g, 5.6 mmol), benzyl trimethyl ammonium chloride (0.04 g, 0.2 mmol) and toluene (50 mL) were added thereto at room temperature, and heated to a temperature of 95-98° C. to react for three days. After cooling to room temperature, the mixture was filtered. The filtrate was washed with saturated aqueous sodium chloride solution twice, added with concentrated hydrochloric acid to form a salt, and then concentrated to dryness to give (S)-5-methoxy-N-propyl-N-(2'-(thien-2-yl-)ethyl)-tetralin-2-amine hydrochloride with a purity of 96% and a yield of 90%.

Example 9

Preparation of Rotigotine (Compound 5)

To a three-necked flask, the (S)-5-methoxy-N-propyl-N-(2'-(thien-2-yl-)ethyl)-tetralin-2-amine (20 g, 61 mmol) prepared above in Example 6 and DCM (300 mL) were added at room temperature, and then cooled to about 0° C. Thereafter, a solution of boron tribromide (73.2 mmol) in dichloromethane (concentration: 1 g/3.8 mL) was added dropwise to the reaction liquid. After the addition, the temperature was warmed up to room temperature to react. After the reaction being complete, the mixture was neutralized by the addition of saturated aqueous sodium bicarbonate solution. The organic phase was separated out and concentrated to give crude rotigotine free base. Yield: 100%, Purity: 91%.

Example 10

Preparation of Rotigotine Hydrochloride

The crude rotigotine (17.2 g) prepared above in Example 9 was dissolved in 100 mL dichloromethane, and adjusted to be acidic by the addition of an aqueous HCl solution or an organic solution of hydrogen chloride or by the introduction of HCl gas. The mixture was filtered and dried to give 18.2 g rotigotine hydrochloride. Yield: 80%, Purity: 98%.

Example 11

Preparation of Rotigotine Hydrochloride

To a 10 L three-necked flask, the (S)-5-methoxy-N-propyl-N-(2'-(thien-2-yl-)ethyl)-tetralin-2-amine hydrochloride (295 g, 0.9 mol) prepared above in Example 7 and 5.5 kg DCM were added at room temperature, and then cooled to a temperature of 0° C.-5° C. Thereafter, a 1 M solution of boron tribromide (1.08 mmol) in dichloromethane (concentration: 1 g/3.8 mL) was added dropwise to the reaction liquid. After the addition, the temperature was warmed up to room temperature to perform the reaction. After the reaction being complete, the mixture was neutralized by the addition of saturated aqueous sodium bicarbonate solution, and left alone and partitioned. The organic phase was adjusted to be acidic by the addition of an aqueous hydrochloride solution or an organic solution of hydrogen chloride or by the introduction of hydrochloride gas. The mixture was filtered, and the filter cake was washed with DCM and dried overnight to give crude rotigotine hydrochloride. Yield: 79.5%, Purity: 98.2%.

Example 12

Purification of Rotigotine Hydrochloride

To a 5 L four-necked reaction flask equipped with a thermometer, a condenser and a mechanical agitator, ethanol (750 mL) was added, and warmed up to 65° C., followed by addition of the above prepared crude rotigotine hydrochloride (500 g, 1.422 mol). The mixture was warmed up to 65° C. and stirred for 40 minutes. After cooling to 45° C., DCM (1500 mL) was added dropwisely, and a large amount of solid were precipitated. After filtration, the filter cake was dried to give 386 g purified rotigotine hydrochloride. Purity: 99.8%, Optical Purity: 99.95%, Yield: 77%.

Example 13

Dissociation of Rotigotine Hydrochloride

To a 10 L four-necked reaction flask equipped with a mechanical agitator and a constant pressure dropping funnel, the above prepared 363 g purified rotigotine hydrochloride and dichloromethane (5475 mL) were added, and neutralized by dropwise addition of 5% aqueous sodium carbonate solution. The organic phase was separated out and washed with water once and concentrated to dryness to give 320 g oil. Hexane (600 mL) was added to the residue to precipitate a solid, which was filtered and dried to give rotigotine solid. Chemical Purity: 99.82%, Optical Purity: 100%, Yield: 98%.

$^1$H-NMR (400 MHz, $CDCl_3$): δ 7.12 (m, 1H, aromatic), 7.0 (m, 1H, aromatic), 6.9 (m, 1H, aromatic), 6.8 (m, 1H, aromatic), 6.7 (m, 1H, aromatic), 6.6 (m, 1H, aromatic), 4.9 (broad double, 1H, —OH), 2.8 (m, 8H, —CH$_2$—, —CH—), 2.6 (m, 3H, —CH$_2$—), 2.10 (m, 1H, —CH$_2$—), 1.5 (m, 3H, —CH$_2$—), 0.9 (t, 3H, —CH$_3$).

The measured optical rotation of the final product is: $[\alpha_d^{20}]$ (C=1, methanol)=−42.7°.

What is claimed is:

1. A chiral compound S-5-substituted-N-2'-(thien-2-yl-)ethyl-tetralin-2-amine represented by the following formula 2, or its chiral acid salts:

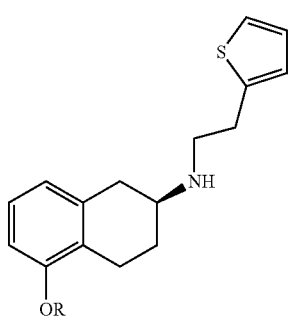

wherein R is C$_1$-C$_6$ lower alkyl or C$_1$-C$_6$ lower fatty acyl.

2. The S-5-substituted-N-2'-(thien-2-yl-)ethyl-tetralin-2-amine or its chiral acid salts according to claim 1, characterized in that R is methyl, ethyl, propyl, isopropyl, or butyl.

3. The S-5-substituted-N-2'-(thien-2-yl-)ethyl-tetralin-2-amine or its chiral acid salts according to claim 1, characterized in that the chiral acid salt is a salt of the S-5-substituted-N-2'-(thien-2-yl-)ethyl-tetralin-2-amine with L-(+)-mandelic acid or L-(+)-tartaric acid.

4. The S-5-substituted-N-2'-(thien-2-yl-)ethyl-tetralin-2-amine or its chiral acid salts according to claim 3, characterized in that the chiral acid salt is a S-5-substituted-N-2'-(thien-2-yl-)ethyl-tetralin-2-amine L-(+)-tartrate represented by the following structure formula:

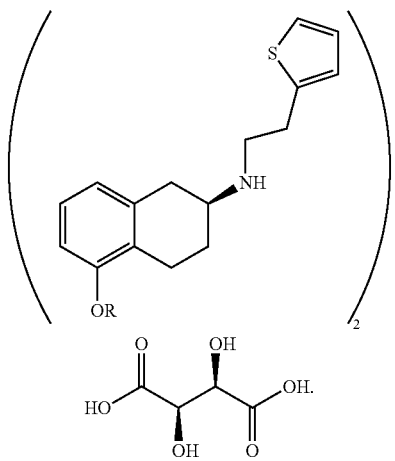

5. A method for preparing the S-5-substituted-N-2'-(thien-2-yl-)ethyl-tetralin-2-amine represented by the formula 2, or its chiral acid salts, comprising:

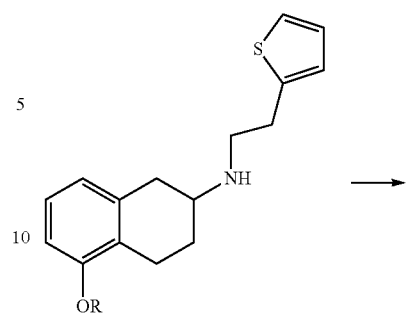

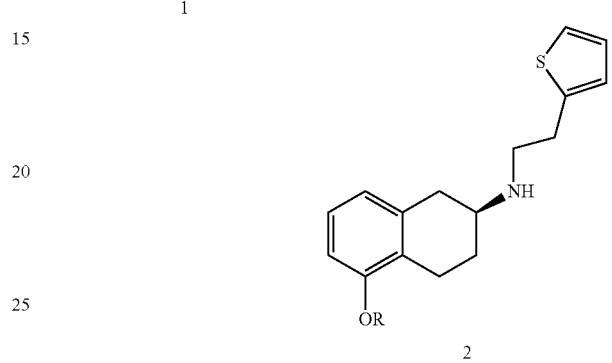

resolving a racemic 5-substituted-N-2'-(thien-2-yl-)ethyl-tetralin-2-amine of formula 1 by using a conventional chiral acid L-(+)-mandelic acid or L-(+)-tartaric acid, to obtain an optically pure chiral acid salt of the 5-substituted-N-2'-(thien-2-yl-)ethyl-tetralin-2-amine of formula 2 in S configuration; and under an alkaline condition, dissociating the chiral acid salt of 5-substituted-N-2'-(thien-2-yl-)ethyl-tetralin-2-amine in S configuration to obtain the optically pure compound of formula 2 in S configuration, wherein R is C$_1$-C$_6$ lower alkyl or C$_1$-C$_6$ lower fatty acyl.

6. The method according to claim 5, characterized in that the step of resolution comprises:

dissolving a racemic 5-substituted-N-2'-(thien-2-yl-)ethyl-tetralin-2-amine of formula 1 in a solvent, wherein the solvent is acetone, methanol, ethanol, water, or a mixed solvent thereof;

dissolving a chiral acid in a solvent to give a solution of the chiral acid, wherein the solvent is acetone, water, or a mixed solvent thereof, and the chiral acid is L-(+)-mandelic acid or L-(+)-tartaric acid; and dropwisely adding the solution of the chiral acid to the solution of the compound for formula 1 at a temperature of 20-30° C., wherein the molar ratio of the chiral acid to the compound of formula 1 is 0.2:1-1:1, and stirring for three hours or more to precipitate a solid, which was filtered and washed to give an optically pure chiral acid salt of the 5-substituted-N-2'-(thien-2-yl-)ethyl-tetralin-2-amine of formula in S configuration.

7. The method according to claim 5, characterized in that the step of dissociation of the chiral acid salt of 5-substituted-N-2'-(thien-2-yl-)ethyl-tetralin-2-amine of formula 2 in S configuration is performed as follows: dissociating the chiral acid salt of the 5-substituted-N-2'-(thien-2-yl-)ethyl-tetralin-2-amine of formula 2 in S configuration with a base in an organic solvent, wherein the base is sodium hydroxide, sodium carbonate or potassium carbonate, and the organic solvent is a mixed solvent system of dichloromethane and water or of ethyl acetate and water.

8. A method for preparing rotigotine using the S-5-substituted-N-2'-(thien-2-yl-)ethyl-tetralin-2-amine of formula 2 or its chiral acid salts, comprising:

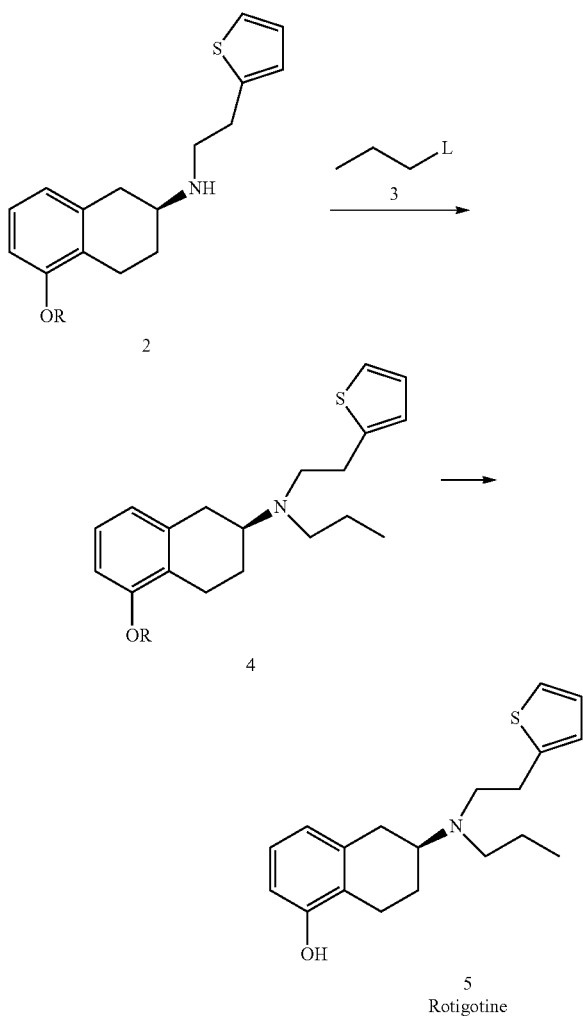

carrying out an alkylation reaction of the S-5-substituted-N-2'-(thien-2-yl-)ethyl-tetralin-2-amine of formula 2 or its chiral acid salt with a compound of formula 3 in a solvent using a base to give compound of formula 4, (S)-5-substituted-N-propyl-N-(2'-(thien-2-yl-)ethyl)-tetralin-2-amine, which can be further salified with an acid; and removing the protecting group R from the compound of formula 4 or its salt to give the compound of formula 5, rotigotine, wherein R is $C_1$-$C_6$ lower alkyl or $C_1$-$C_6$ lower fatty acyl; the compound of formula 3 is propane with a leaving group, L represents the leaving group and is chlorine, bromine, iodine, methylsulfonyl, trifluoromethylsulfonyl, ethylsulfonyl, benzenesulfonyl, tosyl, parachlorobenzenesulfonyl, nitrobenzenesulfonyl or methoxybenzenesulfonyl.

9. The method according to claim 8, characterized in that the solvent used in the alkylation reaction is dichloromethane, toluene, tetrahydrofuran, methyltetrahydrofuran, acetone, butanone, N,N-dimethylformamide, N,N-dimethylacetamide, N-methylpyrrolidone, dimethyl sulfoxide or water; the base is triethylamine, diisopropylethylamine, pyridine, N,N-dimethylaminopyridine, 2,6-dimethylpyridine, N-methylmorpholine, 1,8-diazabicyclo[5.4.0]undec-7-ene, 1,5-diazabicyclo[4.3.0]nonyl-5-ene, sodium carbonate, potassium carbonate, sodium bicarbonate, sodium hydroxide, potassium hydroxide or potassium phosphate.

10. The method according to claim 8, characterized in that a phase transfer catalyst is optionally introduced into the alkylation reaction, wherein the phase transfer catalyst is tetrabutylammonium chloride, tetrabutylammonium bromide, tetrabutylammonium iodide, tetrabutylammonium bisulfate, benzyltrimethylammonium chloride, benzyltriethylammonium chloride, trioctylmethylammonium chloride, 18-crown ether-6 or diphenyl-18-crown ether-6.

11. The method according to claim 8, characterized in that in the step of removing the protecting group R from the compound of formula 4 or its salt to give the compound of formula 5 (rotigotine), a deprotection agent boron tribromide or $AlCl_3$ is added to the organic solution of the compound of formula 4 to perform the reaction at a temperature of $-30°$ C. to room temperature.

12. The method according to claim 8, characterized in that the method further comprises a step of further purifying Rotigotine, wherein Rotigotine is formed into a salt with an acid, and dissociated after the purification to give a purified Rotigotine, wherein the acid is hydrochloric acid, hydrobromic acid, sulphuric acid, phosphoric acid, methanesulfonic acid, 4-methylbenzenesulfonic acid, formic acid, acetic acid, oxalic acid, succinic acid, fumaric acid or maleic acid.

13. The method according to claim 5, characterized in that R is methyl, ethyl, propyl, isopropyl, or butyl.

14. The method according to claim 5, characterized in that the chiral acid salt is a salt of the S-5-substituted-N-2'-(thien-2-yl-)ethyl-tetralin-2-amine of formula 2 with L-(+)-mandelic acid or L-(+)-tartaric acid.

15. The method according to claim 14, characterized in that the chiral acid salt is the S-5-substituted-N-2'-(thien-2-yl-)ethyl-tetralin-2-amine L-(+)-tartrate represented by the following structure formula:

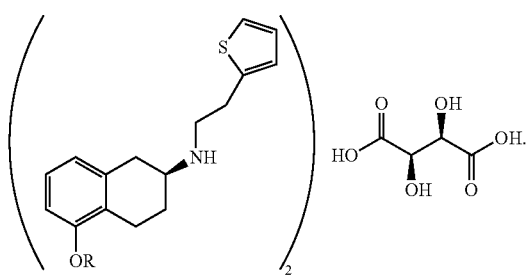

16. The method according to claim 6, wherein the solvent for dissolving the racemic 5-substituted-N-2'-(thien-2-yl-)ethyl-tetralin-2-amine of formula 1 is a mixed solvent of acetone and water with a volume ratio of 1:1 to 10:1.

17. The method according to claim 16, wherein the solvent for dissolving the racemic 5-substituted-N-2'-(thien-2-yl-)ethyl-tetralin-2-amine of formula 1 is a mixed solvent of acetone and water with a volume ratio of 4:1 to 7.5:1.

18. The method according to claim 6, wherein the molar ratio of the chiral acid to the compound of formula 1 is 0.5:1-0.7:1.

19. The method according to claim 8, characterized in that R is methyl, ethyl, propyl, isopropyl, or butyl.

20. The method according to claim 8, characterized in that the chiral acid salt is a salt of the S-5-substituted-N-2'-(thien-2-yl-)ethyl-tetralin-2-amine of formula 2 with L-(+)-mandelic acid or L-(+)-tartaric acid.

21. The method according to claim 20, characterized in that the chiral acid salt is a S-5-substituted-N-2'-(thien-2-yl-)ethyl-tetralin-2-amine L-(+)-tartrate represented by the following structure formula:

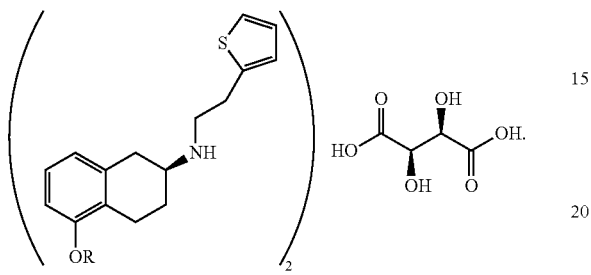

* * * * *